US00PP11622P

United States Patent [19]

Olesen et al.

[11] Patent Number: Plant 11,622

[45] Date of Patent: Nov. 7, 2000

[54] COMPACT FLORIBUNDA ROSE PLANT NAMED 'POULORIN'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/173,861

[22] Filed: Oct. 16, 1998

[51] Int. Cl.[7] ..... A01H 5/00

[52] U.S. Cl. ..... Plt./147

[58] Field of Search ..... Plt./141, 148, 149, Plt./150, 121, 116, 147

*Primary Examiner*—Howard J. Locker

[57] ABSTRACT

A new compact floribunda rose plant which has abundant, salmon-colored flowers and attractive foliage. The variety successfully propagates from softwood cuttings and by traditional budding and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between 'POULmax' and an unnamed seedling. The two parents were crossed and the resulting seeds were planted in a controlled environment. The new variety is named 'POULorin'.

The new rose may be distinguished from its seed parent, 'POULmax', by the following combination of characteristics:

1. 'POULmax' is taller and bushier than 'POULorin'.

2. The flowers of 'POULmax' are more semi-double and larger as compared to the flowers of 'POULorin'.

The new variety may be distinguished from its pollen parent, an unnamed seedling, created by the same inventors, by the following combination of characteristics:

1. The unnamed seedling is a pink miniature rose, while 'POULorin' is a salmon-colored compact floribunda rose.

2. The unnamed seedling is an offspring of Pink Parade 'POULorin' and Concertino.

3. Compared to 'POULorin', the unnamed seedling is a lower, more compact rose with smaller flowers.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULorin' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULorin' was selected by the inventors as a single plant from the progeny of the hybridization in March, 1992.

Asexual reproduction of 'POULorin' by cuttings was first done by L. Pernille and Mogens N. Olesen in their nursery in Fredensborg, Denmark in May, 1993 and by traditional budding in July, 1993. This initial and other subsequent propagations conducted in controlled environments have demonstrated that the characteristics of 'POULorin' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULorin'. Specifically illustrated in SHEET 1:

1. Stem showing branching and the attachment of leaves, buds, and peducles;

2. Flower bud, partially opened bud, and open bloom;

3. Flower petals, detached;

4. Sepals, receptacle, and pedicel;

5. Flowering stem and

6. Leaves.

DETAILED DESCRIPTION OF THE VARIETY

The following is a description of 'POULorin', as observed in its growth in glasshouses in Fredensborg, Denmark, and in a field nursery in Jackson County, Oreg. Color references are made using The Royal Horticultural Society (London, England) Colour Chart, 1995, except where common terms of color are used.

For a comparison, several physical characteristics of the rose variety 'POULskov', a pink floribunda rose variety from the same inventors described and illustrated in U.S. Plant Pat. No. 9,062 and issued on Feb. 28, 1995 are compared to 'POULorin' in Chart 1.

CHART 1

| | 'POULorin' | 'POULskov' |
|---|---|---|
| Petal, upper surface color after opening | Red Group 48C–52C | Red Group 49D–56B |
| Petal, reverse surface color after opening | Red Group 55B–52C | Red Group 55D–56A |
| Basal petal spot, outer side | Yellow Group 5D | Yellow Group 2D–4D |

Parents: 'POULmax'×unnamed seedling.
Classification:
*Botanical.*—*Rosa hybrida.*
*Commercial.*—Compact floribunda.

FLOWER AND FLOWER BUD

Blooming habit: Continuous.
Flower bud:
*Size.*—Upon opening, 25 mm–30 mm in length from base of receptacle to end of bud.
*Bud form.*—Pointed ovoid to high-centered.
*Bud color.*—As sepals unfold, Red Group 55B. Red Group 55B–C at ¼ opening.
*Sepals.*—Green Group 144A. Some sepals with intonations of Greyed-Red Group 179A. Surfaces of sepals slightly pubescent. Few to no stipitate glands present on margins of sepals. Margins lack appendages, but tip of sepal may be feathered. These longer sepals are 35–40 mm in length.
*Receptacle.*—Surface: Smooth, glabrous. Shape: Urn-shaped. Size: Medium. 6 mm (h)×6 mm (w). Color: Green Group 138A–B. On plants grown under high light conditions, receptacles may exhibit intonations of Greyed-Red Group 184A.
*Peduncle.*—Surface: Smooth, glabrous. Length: 45 mm to 50 mm average length. Color: Green Group 138B with intonations of Greyed-Red Group 179A. Strength: Upright to semi-upright.
*Borne.*—Singly and in small clusters.
Flower bloom:
*Fragrance.*—Weak floral scent.
*Duration.*—As a pot plant, flowers last from 8 to 11 days. As a cut flower 6 to 8 days. Petals fall cleanly away from plant.
*Size.*—Medium-large for a 15 cm pot rose. Average flower diameter is 50–60 mm when open.
*Form.*—Shape of flower when viewed from the side: Upon opening, upper part: Flat to flattened convex. Upon opening, lower part: Flattened convex. Open flower, upper part: Flattened convex. Open flower, lower part: Flat.
*Petalage.*—Semi-double. Average range: 15–20 under normal conditions with few to no petalpoids.
Color:
*Upon opening, petals.*—Petals: Upper Surface: Red Group 48C–52C. Reverse Side: Red Group 55B.
*Upon opening, basal petal spots.*—Petals: Outer Side: Yellow Group 5C. Inner Side: Yellow Group 7B.
*Upon opening, petals.*—Petals: Upper Surface: Red Group 48C–52C. Reverse Side: Red Group 55B–52C.
*Upon Opening, basal petal spots.*—Petals: Outer Side: Yellow Group 5D. Inner Side: Yellow Group 7C.
General tonality: On open flower Red Group 48C–52C. No change in the general tonality at the end of the third day. Afterwards, general tonality is Red Group 48D–52D.
Petals:
*Petal reflex.*—Interior petals reflex slightly.
*Petal edge.*—Generally uniform with point in center of margin.
*Shape.*—Rounded deltoid.
*Petaloids.*—Commonly none.
*Thickness.*—Average.
*Arrangement.*—Informal.

Reproductive organs:
*Pollen.*—Color: Yellow Group 12C. Abundance: Average.
*Anthers.*—Size: Small. Color: Early: Yellow Group 5C. Late: Greyed-Orange Group 175A. Abundance: Above average abundance.
*Filaments.*—Color: Yellow-Green Group 150C.
*Stigmas.*—Stigmas generally superior to anthers. Color: Green-White Group 157A.
*Styles.*—Color: Green-White Group 157A.
*Hips.*—None observed.

PLANT

Plant growth: Vigorous, compact, upright to bushy. When grown as a 15 cm pot plant, the average height of the plant itself is 22 to 24 cm and the average width is 22 cm. When grown as an own-root plant in the nursery, the average height of the plant itself is 60 to 70 cm and the average width is 50 to 60 cm.
Stems:
*Color.*—Young wood: Green-White Group 143A. Older wood: Green-White Group 143A.
*Prickles.*—Incidence: Moderate. Size: Average length: 7 mm–8 mm. Range 5–9. Color: Yellow-Green Group 145B–C with intonations of Greyed-Red Group 179A. Shape: Broadly linear to deeply concave.
*Surface.*—Young wood: Smooth. Older wood: Smooth.
Plant foliage: Normal number of leaflets on normal leaves in middle of the stem: 5–7 leaflets.
*Leaf size.*—110 mm (l)×55 mm (w) average.
*Abundance.*—Above average abundance.
*Color.*—Upper Leaf Surface: Green Group 137B. Lower Leaf Surface: Green Group 138B–146C. Juvenile foliage: Green Group 138A. Anthocyanin intonation: Strong. Location: Upper and lower surfaces of leaflets, leaflet margins, stems, leaf petioles, and leaf rachis. Color: Greyed-Red Group 180B.
Plant leaves and leaflets:
*Stipules.*—Tips of stipules generally parallel to petiole. Size: 14 mm–16 mm. Color: Green Group 137C. Stipitate glands: Present. Moderate numbers on stipule margins.
*Petiole.*—Length: 15 mm–20 mm. Color: Green Group 137C. Underneath: With small prickles and limited stipitate glands. Margins: With limited numbers of stipitate glands.
*Rachis.*—Color: Green Group 137C. Underneath: With small prickles and limited numbers of stipitate glands. Margins: With limited numbers of stipitate glands.
*Leaflet.*—Edge: Serrated. Shape: Ovate.
*Other.*—Glossy finish and leathery texture.
Disease resistance: Above average resistance to mildew, black spot, and Botrytis under outdoor growing conditions in Jackson County, Oreg.

We claim:

1. A new and distinct variety of rose plant of the compact floribunda class, substantially as herein illustrated and described as a distinct and novel rose variety due to its abundant, salmon-colored flowers, vigorous and compact growth, year round flowering under glasshouse conditions, suitability for production from softwood cuttings and by traditional budding, and durable flowers and foliage which make the variety suitable for distribution in the floral industry.

* * * * *

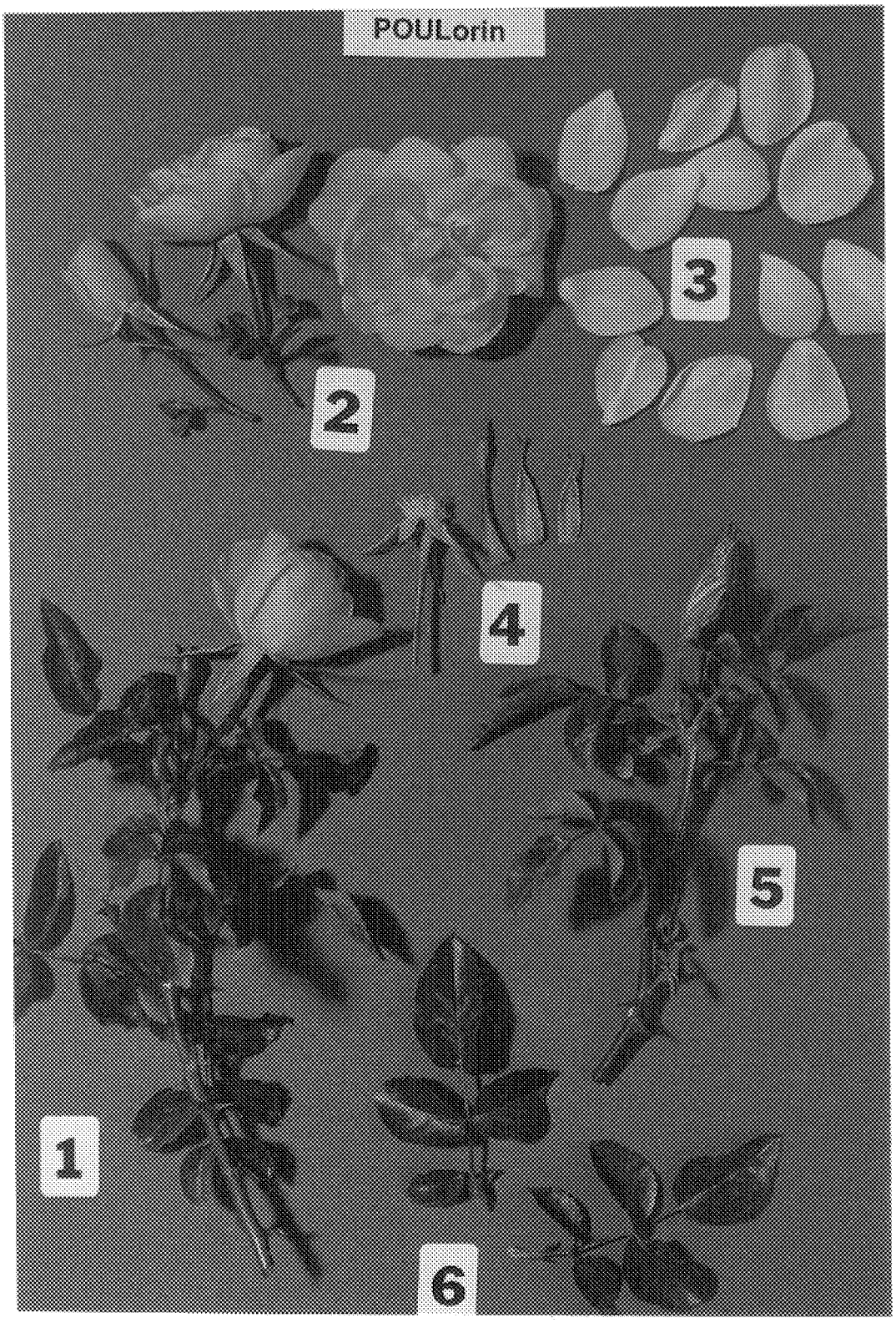
POULorin
1
2
3
4
5
6